US006552341B1

(12) United States Patent
Desplats et al.

(10) Patent No.: US 6,552,341 B1
(45) Date of Patent: Apr. 22, 2003

(54) INSTALLATION AND METHOD FOR MICROSCOPIC OBSERVATION OF A SEMICONDUCTOR ELECTRONIC CIRCUIT

(75) Inventors: Romain Desplats, Toulouse (FR); Bruno Benteo, Pompertuzat (FR)

(73) Assignee: Centre National d'Etudes Spatiales, Paris (FR)

( * ) Notice: Subject to any disclaimer, the term of this patent is extended or adjusted under 35 U.S.C. 154(b) by 18 days.

(21) Appl. No.: 09/684,436

(22) Filed: Oct. 10, 2000

(30) Foreign Application Priority Data

Apr. 9, 1999 (FR) .............................. 99 04479

(51) Int. Cl.[7] .............................................. G02B 21/00
(52) U.S. Cl. ..................... 250/311; 250/310; 250/237.2; 250/237.4; 250/237.5; 350/507; 350/520; 350/523; 350/529; 356/72; 356/237.25
(58) Field of Search ................................. 250/311, 310, 250/237.4, 237.5, 237.2; 356/237.4–237.5, 237.2–237.3, 72, 237.25; 350/507, 520, 523, 529

(56) References Cited

U.S. PATENT DOCUMENTS 4,537,477 A * 8/1985 Takagi et al. ............... 350/507
5,220,403 A * 6/1993 Batchelder et al. ......... 356/345
5,483,065 A * 1/1996 Sato et al. ................... 250/310

FOREIGN PATENT DOCUMENTS

| DE | 33 07 745 A1 | 9/1983 |
| EP | 61168853 | 7/1986 |
| EP | 06283127 | 10/1994 |
| EP | 10214583 | 8/1998 |

* cited by examiner

Primary Examiner—Bruce Anderson
Assistant Examiner—Zia R. Hashmi
(74) Attorney, Agent, or Firm—Young & Thompson

(57) ABSTRACT

The installation for microscopic observation of a semiconductor electronic circuit includes, in a vacuum, a reflection particle interaction microscope and parts for supporting the circuit facing the reflection particle interaction microscope. The installation further includes a reflection optical microscope including optical observation part and elements for illuminating the circuit to be observed, with the illumination elements and the optical observation part on the same side of the circuit and the reflection optical microscope and the reflection particle interaction microscope disposed face-to-face on a common observation axis on respective opposite sides of the circuit.

7 Claims, 2 Drawing Sheets

INSTALLATION AND METHOD FOR MICROSCOPIC OBSERVATION OF A SEMICONDUCTOR ELECTRONIC CIRCUIT

BACKGROUND OF THE INVENTION

The present invention relates to an installation for microscopic observation of a semiconductor electronic circuit, of the type which includes, in an evacuated observation enclosure (12):

a reflection particle interaction microscope;

means for supporting the circuit facing the reflection particle interaction microscope, and means for causing relative movement between the circuit and the reflection particle interaction microscope.

DESCRIPTION OF THE RELATED ART

It is essential to verify the quality of a semiconductor circuit, also commonly referred to as an integrated circuit, and that it is operating correctly, during or after its fabrication.

Integrated circuits are therefore observed while they are still joined together in a wafer of silicon or some other substance in which they have been etched side-by-side.

An initial observation is carried out using a reflection optical microscope to detect large defects, such as particles fouling the surface of the circuits.

The increasing complexity of the circuits and the decreasing size of their components make it necessary to use a scanning electron microscope or some other type of reflection particle interaction microscope to show up defects that cannot be detected by an optical microscope.

Because of its very high resolution, the scanning electron microscope is satisfactory for detecting small defects or impurities.

In addition to using a scanning electron microscope to detect defects, it is possible to stimulate the integrated circuit electrically, either directly or by induction, and to observe a localized area of the integrated circuit to detect and therefore measure variations in the signal with time.

In the case of an optical microscope, it is possible to observe and to measure the operation of the circuits by analyzing the signal reflected through the substrate (which is made of silicon, for example) from the bottom of the circuit or through the oxide from the top of the circuit.

In the case of a reflection particle interaction microscope, the reflected signal gives information on the electric signals flowing in the metal tracks that cover the surface of the circuit.

The scanning electron microscope has a very narrow field of view. Positioning it relative to the extremely large surface of the electronic circuit is therefore difficult. Similarly, the exact location of the observed area of the circuit relative to the circuit as a whole is difficult to determine because of the narrow field of view.

SUMMARY OF THE INVENTION

An object of the invention is to facilitate determining the location of the observation area, verifying a circuit in a microscopic observation installation which can detect small defects and analysing circuits made up of very small components.

To this end, the invention provides an installation for microscopic observation of a semiconductor electronic circuit, of the aforementioned type, characterized in that it includes, in said enclosure, a reflection optical microscope including optical observation means and means for illuminating the circuit, with the illumination means and the optical observation means on the same side of the circuit and the reflection optical microscope and the reflection particle interaction microscope disposed face-to-face on a common observation axis on respective opposite sides of the circuit carried by the support means, and in that it includes means for causing relative movement between the circuit and the reflection optical microscope identical to the relative movement between the circuit and the reflection particle interaction microscope so that the two microscopes are kept facing each other along the same observation axis and observe the same region of the circuit.

In one particular embodiment, the installation includes one or more of the following features:

the illumination means include a source of near infrared or ultraviolet radiation;

the reflection particle interaction microscope is at least one of the following: a scanning electron microscope, an ion beam microscope, an electron beam tester and a focussed ion beam system;

the reflection optical microscope is equipped with a laser beam measurement and observation system;

the means for supporting the object to be observed include a frame adapted to position the semiconductor circuit with its etched face towards the reflection particle interaction microscope and its face consisting of non-etched substrate towards the reflection optical microscope;

the means for producing relative movement between the circuit and each of the two microscopes include means for moving the circuit relative to the enclosure in a plane perpendicular to the common observation axis of the two microscopes;

the means for supporting the circuit are fixed relative to said enclosure and the means for causing relative movement between the circuit and each of the two microscopes include, for each microscope, means for moving the microscope relative to said enclosure in a plane perpendicular to the common observation axis of the microscopes, and in that it further includes laser interferometer means for aligning the two microscopes disposed between them.

The invention also provides method of microscopic observation of a semiconductor electronic circuit placed in an evacuated observation enclosure, the method including the steps of:

observing a first face of the circuit using a reflection particle interaction microscope; and causing relative movement between the circuit and the reflection particle interaction microscope; characterized in that it further includes the steps of:

observing the face of the circuit opposite said first face using a reflection optical microscope which is disposed face-to-face with the reflection particle interaction microscope on a common observation axis and on the other side of the circuit by illuminating the opposite face of the circuit with illuminating means facing the opposite face of the circuit; and causing relative movement between the circuit and the reflection optical microscope identical to the relative movement between the circuit and the reflection particle interaction microscope so that the two microscopes are kept facing each other along the same observation axis and observe the same region of the circuit.

BRIEF DESCRIPTION OF THE DRAWINGS

The invention will be understood better after reading the following description, which is given by way of example only and with reference to the accompanying drawings, in which.

DESCRIPTION OF THE PREFERRED EMBODIMENTS

Figure 1:
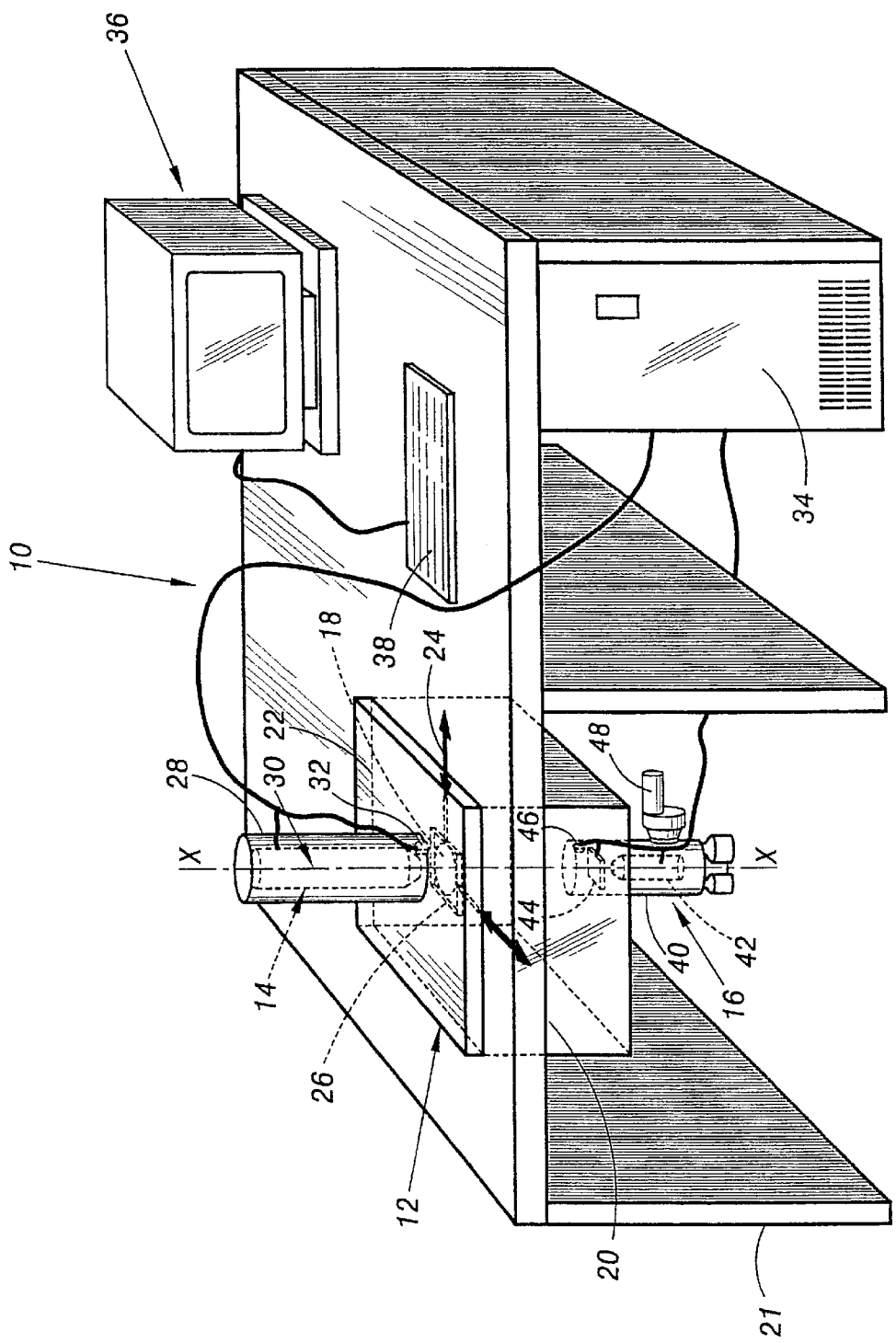
FIG. 1 is a diagrammatic perspective view of an observation installation according to the invention.

The installation shown in FIG. 1 is for microscopic observation of a silicon wafer on which a set of semiconductor circuits has been etched. The observation can take the form of a measurement which involves monitoring changes in the detected signal with time.

The observation installation includes an evacuated observation enclosure 12 on respective opposite sides of which are disposed a reflection optical microscope 14 and a reflection particle interaction microscope 16, for example a scanning electron microscope.

The optical microscope 14 and the scanning electron microscope 16 are disposed face-to-face on a common observation axis X—X and on respective opposite sides of the specimen 18 consisting of the wafer carrying the circuits to be observed.

The observation enclosure 12 is defined by a substantially parallelepipedal hermetically sealed enclosure 20. The enclosure 20 and the microscopes 14 and 16 are carried by a frame 22. The two microscopes are rigidly connected to the enclosure 20 so that they can be held with their observation axes exactly coincident.

The enclosure 20 is open at the top. It is closed by a hermetically sealed cover 22. The enclosure 20 contains means 24 for moving the specimen 18 in a plane perpendicular to the common observation axis X—X of the two microscopes, in particular in two perpendicular directions in that plane.

The means 24 include a conductive material frame 26 inside which the specimen 18 is supported so that its two main faces are exposed. The specimen 18 is electrically connected to the frame 26 to evacuate surface charges.

The cover 22 supports the reflection optical microscope 14 which is housed in a sealed cylindrical chamber 28 facing the specimen 18.

It includes optical observation and/or measuring means 30, consisting of a video camera with an appropriate lens, for example. The optical microscope 14 further includes means 32 for illuminating the specimen 18 disposed on the same side of the specimen as the observation means 30.

The illuminating means 32 include a source of radiation suited to the type of observation required. For example, for observing and measuring signals in a circuit, a light source emitting in the near infra-red is chosen. This generally corresponds to a wavelength of approximately 1 $\mu$m. Infrared radiation can pass through the silicon and then be reflected.

The observation means 30 are a few millimetres away from the face of the electronic circuit to be observed.

The optical microscope 14 is connected to a data processing unit 34 in the form of a computer running an appropriate program. Display means 36 such as a display screen and control means 38 such as a keyboard are provided for controlling the data processing unit 34 and the operation of the two microscopes.

The scanning electron microscope 16 is fixed along the axis X—X under the bottom of the enclosure 20 on the side opposite the cover 12. It is received into a cylindrical chamber 40 opening into the interior of the enclosure opposite the specimen 18.

As is known in the art, the scanning electron microscope 16 includes an electron gun 42 at the output from which is an electronic lens 44 for focusing the electrons onto the specimen 18. It further includes a detector for detecting electrons reflected by the surface of the specimen 18.

The electron gun 42 and the detector 46 are connected to the data processing unit 34 to generate an image on the screen 36 or a measurement.

A vacuum system 48 is connected to the chamber 40 housing the scanning electron microscope. The system is adapted to create a sufficiently hard vacuum in the enclosure 12 and in the chambers 28 and 40 communicating with it.

The frame 26 is advantageously adapted to support the specimen 18 so that the semiconductor electronic circuits face the scanning electron microscope 16 and their rear face, consisting essentially of silicon, faces the optical microscope 14.

Because the two microscopes 14 and 16 are colinear, to analyze a given area of an electronic circuit it is clearly possible to locate that area by moving the specimen 18 and observing its rear face using the optical microscope 14. Once the specimen 18 has been positioned correctly, the area in question of the specimen can be observed precisely using the scanning electron microscope 16, which observes the opposite face of the same portion of the electronic circuit.

The field of view of the optical microscope 14 is 10 to 100 times greater than that of the scanning electron microscope, which facilitates locating the area to be observed compared to locating it using a scanning electron microscope alone.

The optical image is obtained from the rear face of the electronic circuit. In the case of silicon, for example, this is made possible by an appropriate choice of the wavelength of the radiation used for illumination. Radiation in the near infrared penetrates the silicon and is reflected from the metal oxide tracks. A system of this kind is also suitable for observing the operation of a circuit by measuring variations in the reflected signal.

In a similar manner, if the circuit is turned over, an optical image of the front face can be obtained with excellent resolution by choosing light source emitting ultraviolet radiation.

Figure 2:
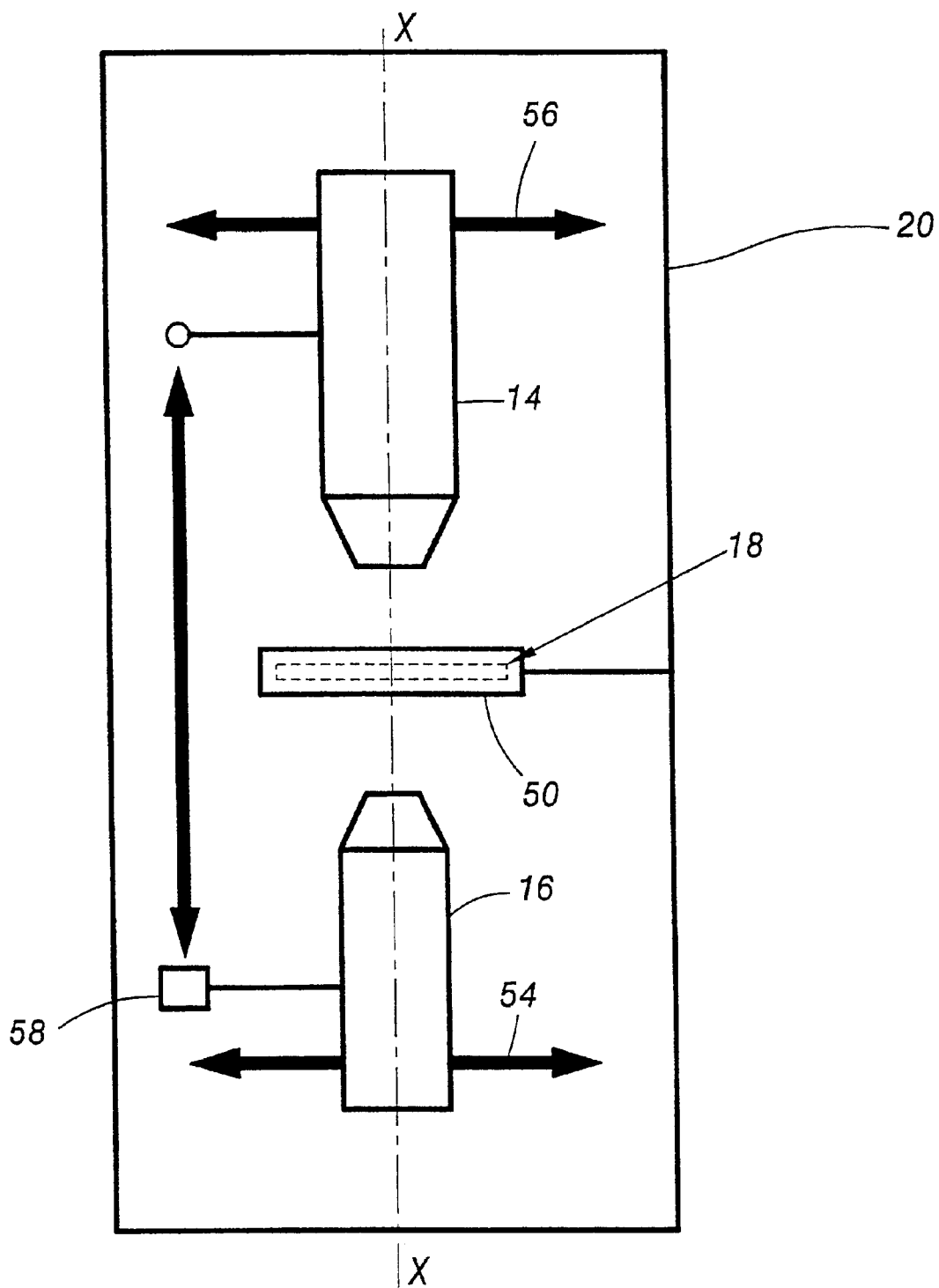
FIG. 2 is a diagrammatic elevation of a variant of the installation from FIG. 1.

FIG. 2 shows a variant of an installation according to the invention.

In this variant, the same components are designated by the same reference numbers.

Although in the FIG. 1 embodiment the microscopes 14 and 16 are fixed relative to the observation enclosure 12 and the specimen 18 is mobile, in the FIG. 2 embodiment the microscopes 14 and 16 are mobile relative to the enclosure 12 and the specimen 18 is supported by a support 50 which is either fixed or mobile relative to the enclosure.

Each microscope 14, 16 is therefore associated with its own respective means 54, 56 for moving it in a plane perpendicular to its observation axis. The observation axes of the two microscopes are parallel.

The means 54, 56 for moving the two microscopes are synchronized so that the observation axes of the two microscopes coincide. This is known in the art.

Laser interferometer means 58 are disposed between the two microscopes and the specimen to align the axes of the two microscopes correctly.

Interferometer means can measure the displacement between two members with an accuracy much better than one micron. This is known in the art. It is therefore possible to determine mechanical positioning errors between the microscopes and the specimen and to compensate it by modifying the area scanned by one or both microscopes. In this kind of configuration the three components consisting of the two microscopes and the specimen can be aligned with more than adequate precision.

The interferometer means 58 can detect any misalignment between the axes of the microscopes. This is known in the art. They then command the means 54, 56 for moving the microscopes to compensate the detected error.

In either embodiment, the reflection optical microscope is advantageously equipped with laser beam measuring means which can observe the operation of a circuit from its rear face, among other things. In the case of silicon, for example, the chosen light source emits in the near infrared. Because silicon is transparent to radiation in the near infrared, it is possible to observe the relative phase difference between the incident radiation and the reflected radiation and how it varies with time and to represent the variation in the form of measurements corresponding to the operation of the circuit.

Similarly, the scanning electron microscope is advantageously equipped with electron beam test means which can analyze the circuit while it is operating, electrons impinging on the circuit being reflected along different trajectories according to the potential on each track of the circuit. In this case, observation is localized and the variations in the detected signal with time are observed. It is therefore possible to measure variations in the potential contrast for a track of a circuit, for example, and to trace the evolution of voltage levels with time. Modern electron beam testers can achieve accuracies much better than one volt and one microsecond.

The optical microscope is advantageously also equipped with a device for emitting a laser beam for modifying the circuit by ablation or by depositing material in the presence of a suitable gas.

Similarly, the scanning electron microscope can be replaced by a focused ion beam system. In this case, the electron source is replaced by an ion source. The primary ion beam causes secondary particles (electrons or ions) to be emitted from the surface of the specimen. Just as with the scanning electron microscope, variations in the detected secondary electrons can be observed for imaging or measurement. Alternatively, the focussed ion beam system can be equipped with a system for detecting secondary ions, in which case it is referred to as a secondary ion microscope. The focused ion beam system is advantageously equipped with a system for treating the circuit with a focussed beam of ions, using the ion beam to cut selected tracks of the circuit, or to deposit material on the circuit if the ion beam is applied in the presence of a plasma generated by feeding a gas onto the beam scanning axis. The gas is then subject directly to the effect of the beam and behaves like a localized plasma. Depending on the nature of the gas and the energy of the ion beam, it is possible to excavate or to cut the material on the surface of the circuit or to deposit a material, for example a metal.

What is claimed is:

1. An installation (10) for microscopic observation of a semiconductor electronic circuit (18), which installation includes, in an evacuated observation enclosure (12):
    a reflection particle interaction microscope (16);
    means (26; 50) for supporting the circuit (18) facing the reflection particle interaction microscope (16), and
    means (24; 54) for causing relative movement between the circuit (18) and the reflection particle interaction microscope (16), characterized in that it includes, in said enclosure (12), a reflection optical microscope (14) including optical observation means (30) and means (32) for illuminating the circuit (18), with the illumination means (32) and the optical observation means (30) on the same side of the circuit (18) and the reflection optical microscope (14) and the reflection particle interaction microscope (16) disposed face-to-face on a common observation axis on respective opposite sides of the circuit (18) carried by the support means (26), in that it includes means (24; 56) for causing relative movement between the circuit (18) and the reflection optical microscope (14) identical to the relative movement between the circuit (18) and the reflection particle interaction microscope (16) so that the two microscopes are kept facing each other along the same observation axis and observe the same region of the circuit (18), and in that the means (26) for supporting the object to be observed include a frame (26) adapted to position the semiconductor circuit (18) with its etched face towards the reflection particle interaction microscope (16) and its face consisting of non-etched substrate towards the reflection optical microscope (14).

2. An installation according to claim 1, characterized in that the illumination means (32) include a source of near infrared or ultraviolet radiation.

3. An installation according to claim 1, characterized in that the reflection particle interaction microscope (16) is at least one of the following: a scanning electron microscope, an ion beam microscope, an electron beam tester and a focussed ion beam system.

4. An installation according to claim 1, characterized in that the reflection optical microscope (14) is equipped with a laser beam measurement and observation system.

5. An installation according to any preceding claim, characterized in that the means for producing relative movement between the circuit (18) and each of the two microscopes (14, 16) include means (24) for moving the circuit (18) relative to the enclosure (12) in a plane perpendicular to the common observation axis of the two microscopes (14, 16).

6. An installation according to any of claims 1 to 4, characterized in that the means (50) for supporting the circuit (18) are fixed relative to said enclosure (12) and the means for causing relative movement between the circuit (18) and each of the two microscopes include, for each microscope, means (54, 56) for moving the microscope (14, 16) relative to said enclosure (12) in a plane perpendicular to the common observation axis of the microscopes, and in that it further includes laser interferometer means (58) for aligning the two microscopes (14, 16) disposed between them.

7. A method of microscopic observation of a semiconductor electronic circuit (18) placed in an evacuated observation enclosure (12), the method including the steps of:

observing a etched face of the circuit (18) using a reflection particle interaction microscope (16); and causing relative movement between the circuit (18) and the reflection particle interaction microscope (16); characterized)in that it further includes the steps of:

observing the opposite face of the circuit (18) consisting of non-etched substrate using a reflection optical microscope (14) which is disposed face-to-face with the reflection particle interaction microscope (16) on a common observation axis and on the other side of the circuit (18) by illuminating the opposite face of the circuit (18) with illuminating means (32) facing the opposite face of the circuit (18); and causing relative movement between the circuit (18) and the reflection optical microscope (14) identical to the relative movement between the circuit (18) and the reflection particle interaction microscope (16) so that the two microscopes (14, 16) are kept facing each other along the same observation axis and observe the same region of the circuit (18).

* * * * *